United States Patent [19]

Kawashima et al.

[11] Patent Number: 4,742,817
[45] Date of Patent: May 10, 1988

[54] ENDOSCOPIC APPARATUS HAVING A BENDABLE INSERTION SECTION

[75] Inventors: Masahiro Kawashima; Yasuhiro Ueda, both of Tokyo, Japan

[73] Assignee: Olympus Optical Co., Ltd., Japan

[21] Appl. No.: 854,823

[22] Filed: Apr. 23, 1986

[30] Foreign Application Priority Data

May 15, 1985 [JP] Japan .................. 60-103408
Jul. 25, 1985 [JP] Japan .................. 60-164904

[51] Int. Cl.⁴ ............................................. A61B 1/00
[52] U.S. Cl. ............................................. 128/4
[58] Field of Search ................. 128/3, 4, 5, 6, 7, 8, 128/657, 772

[56] References Cited

U.S. PATENT DOCUMENTS

| | | | |
|---|---|---|---|
| 1,880,551 | 10/1932 | Wappler | 128/7 |
| 3,552,384 | 1/1971 | Pierie et al. | |
| 3,854,473 | 12/1974 | Matsuo | 128/8 |
| 4,292,961 | 10/1981 | Kawashima | 128/6 |
| 4,427,000 | 1/1984 | Ueda | 128/6 |
| 4,456,017 | 6/1984 | Miles | 128/772 |
| 4,607,622 | 8/1986 | Fritch et al. | 128/6 |

FOREIGN PATENT DOCUMENTS 2950792 12/1979 Fed. Rep. of Germany .
58-23105 5/1983 Japan .

*Primary Examiner*—William H. Grieb

[57] ABSTRACT

An endoscopic apparatus includes an insertion section extending from an operating section and having a channel extending from the operating section to the distal end of the insertion section. The insertion section is adapted to be bent in a predetermined direction. A sheath is removably inserted into the channel and has a bendable portion located in the distal end portion of the insertion section. The bendable portion is remotely bent by an operating mechanism from the operating section to bend the distal end portion of the insertion section. The sheath is positioned in the insertion channel by a positioning mechanism so that the bendable portion is bent in the predetermined direction.

18 Claims, 4 Drawing Sheets

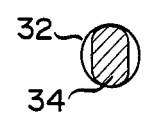
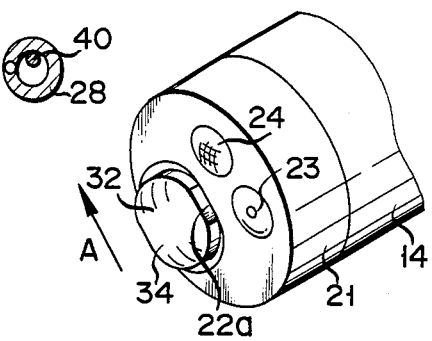
FIG. 4  FIG. 5  FIG. 6
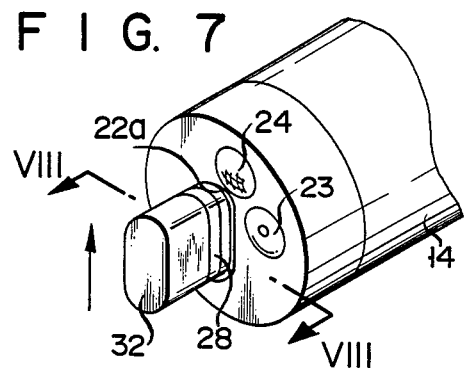
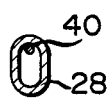
FIG. 7  FIG. 8
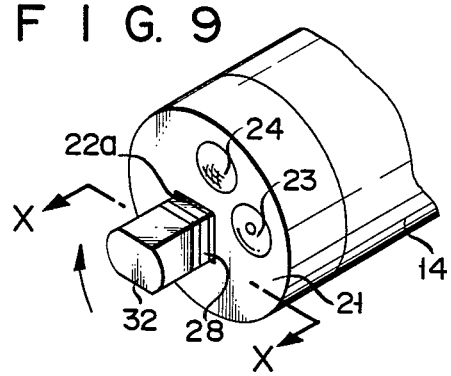
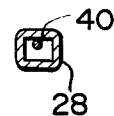
FIG. 9  FIG. 10

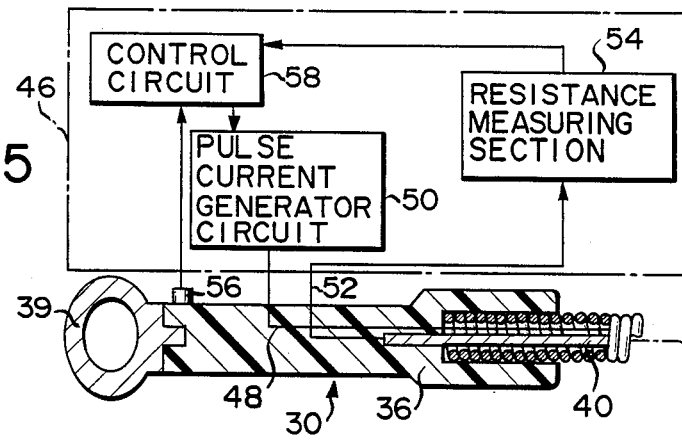
F I G. 15
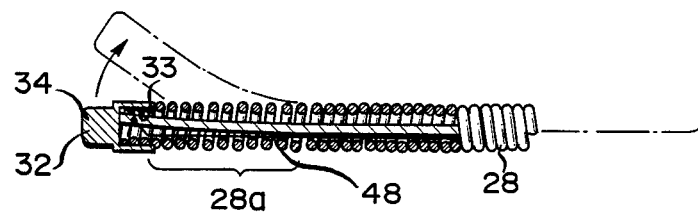
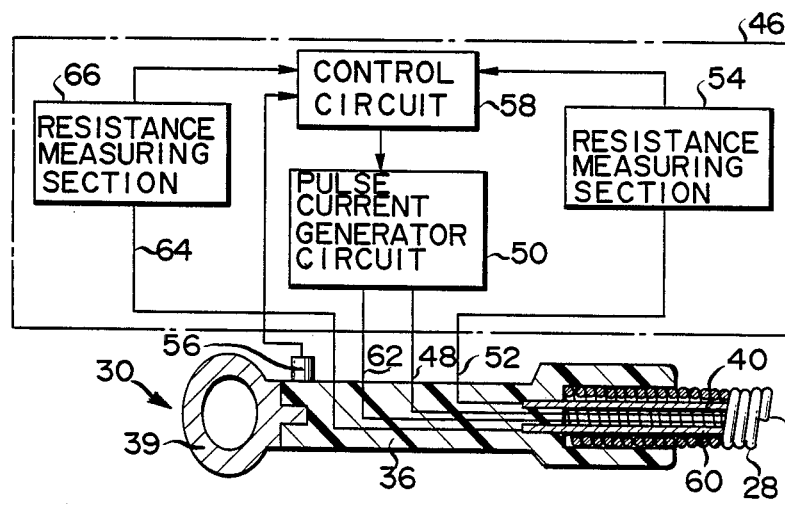
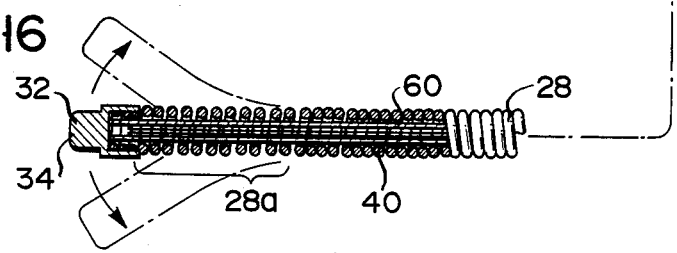
F I G. 16

ENDOSCOPIC APPARATUS HAVING A BENDABLE INSERTION SECTION

BACKGROUND OF THE INVENTION

The present invention relates to an endoscopic apparatus with a bendable insertion section.

In general, an endoscope comprises an operating section and an insertion section extending therefrom. The insertion section has a bendable portion near its distal end portion such that its distal end can be bent in a desired direction. The bendable portion is remotely operated from the operating section by means of an operating wire. It is formed of an articulated mechanism which includes a plurality of cylinders rotatably coupled to one another.

Endoscopes have recently started to be used in the treatment of various internal organs, so that their insertion section is increasingly expected to be reduced in diameter. If the insertion section, however, is provided with a bendable portion including such an articulated mechanism as aforesaid, its diameter cannot be reduced below a fixed value. If a very thin insertion section is needed, therefore, the articulated mechanism or other bending mechanism must inevitably be removed from the section. In this case, however, the distal end portion of the insertion section cannot be bent in a desired direction.

In the field of vascular catheters, an arrangement has been proposed such that a stylet having a bendable distal end portion is inserted into a catheter, and the distal end portion of the catheter is bent by bending that of the stylet. The distal end portion of the insertion section of an endoscope may be bent by means of this mechanism. Namely, the stylet may be inserted into a channel of the insertion section so that the distal end portion of the insertion section is bent as that of the stylet is bent.

However, the bending direction of the stylet relative to the insertion section of the endoscope varies with the state of the stylet in the channel. Therefore, the bending direction of the distal end portion of the insertion section, which follows the stylet, cannot be foreseen before the stylet is bent actually. Thus, the distal end portion of the insertion section cannot accurately be bent in the desired direction. For example, it may possibly be bent in a direction such that optical fibers in the insertion section break.

SUMMARY OF THE INVENTION

The present invention is contrived in consideration of these circumstances, and is intended to provide an endoscopic apparatus in which the insertion section is reduced in diameter and its distal end portion can be bent in a desired direction.

In order to achieve the above object, according to the present invention, there is provided an endoscopic apparatus which comprises an operating section; a flexible insertion section extending from the operating section and adapted to be inserted into the body cavity and bent in a predetermined direction, the insertion section including a channel extending from the operating section to the distal end of the insertion section; a stylet including a sheath removably inserted in the channel and extending to the distal end of the insertion section, the sheath having a bendable portion located in the distal end portion of the insertion section, and operating means for remotely bending the bendable portion of the sheath from the operating section side to bend the distal end portion of the insertion section; and positioning means for positioning the sheath in the insertion section so that the bendable portion is bent in the predetermined direction.

BRIEF DESCRIPTION OF THE DRAWINGS

FIGS. 1 to 6 show an endoscopic apparatus according to a first embodiment of the present invention, in which FIG. 1 is a plan view of an endoscope body, FIG. 2 is a front view of a distal end face of an insertion section, FIG. 3 is a sectional view of a stylet, FIG. 4 is a sectional view taken along line IV—IV of FIG. 3, FIG. 5 is a sectional view taken along line V—V of FIG. 3, and FIG. 6 is a perspective view of the distal end portion of the insertion section showing a state that the stylet is inserted in a channel;

FIGS. 7 and 8 show a second embodiment of the invention, in which FIG. 7 is a perspective view of the distal end portion of an insertion section with a stylet inserted therein, and FIG. 8 is a sectional view taken along line VIII—VIII of FIG. 7;

FIGS. 9 and 10 show a third embodiment of the invention, in which FIG. 9 is a perspective view of the distal end portion of an insertion section with a stylet inserted therein, and FIG. 10 is a sectional view taken along line X—X of FIG. 9;

FIGS. 11 and 12 show a fourth embodiment of the invention, in which FIG. 11 is a perspective view of the distal end portion of an insertion section with a stylet inserted therein, and FIG. 12 is a sectional view taken along line XII—XII of FIG. 11;

FIGS. 13 and 14 show a fifth embodiment of the invention, in which FIG. 13 is a sectional view of a stylet, and FIG. 14 is a sectional view taken along line XIV—XIV of FIG. 13;

FIG. 15 is a sectional view of a stylet according to a sixth embodiment of the invention; and FIG. 16 is a sectional view of a stylet according to a seventh embodiment of the invention.

DETAILED DESCRIPTION OF THE PREFERRED EMBODIMENTS

Preferred embodiments of the present invention will now be described in detail with reference to the accompanying drawings.

Figure 1:
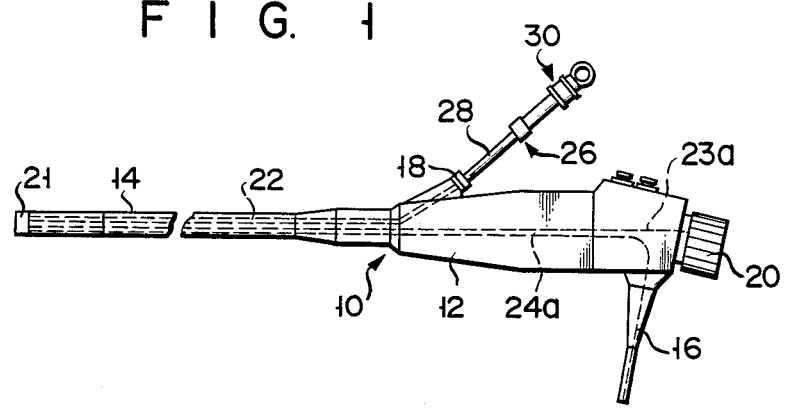
Figure 2:
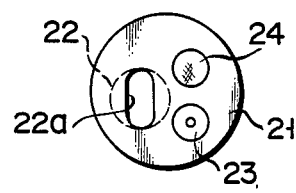
Figure 3:
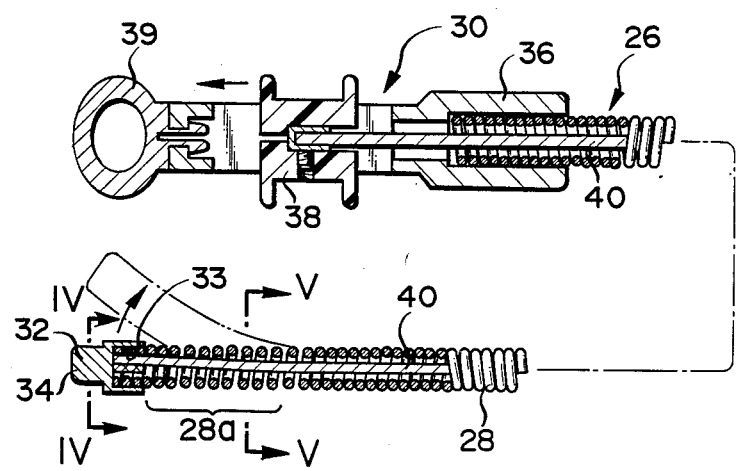

FIGS. 1 to 6 show an endoscopic apparatus according to a first embodiment of the invention. As shown in FIG. 1, endoscope body 10 includes operating section 12, insertion section 14, and universal cord 16. Section 14 and cord 16 both extend from section 12. Section 12 is provided with inlet port 18 and eyepiece portion 20. Section 14, which is formed of a flexible tube, is fitted with rigid distal member 21 at its distal end. Channel 22 extends through insertion section 14. One end of channel 22 connects with port 18, while the other end opens to the distal end face of member 21. As shown in FIG. 2, the distal end face of member 21 is formed with channel opening 22a, view window 23, and illumination window 24. Window 23 is optically connected to eyepiece portion 20 by means of image guide 23a formed of optical fibers. Window 24 is connected to light guide 24a which extends through cord 16 and sections 12 and 14. Opening 22a, connecting with channel 22, is in the form of a vertically elongated oval, as shown in FIG. 2. Channel 22 has a circular cross section throughout its length, and its inside diameter is equal to the length of the major axis of opening 22a.

As shown in FIGS. 3 to 6, the endoscopic apparatus comprises stylet 26 for bending the distal end portion of insertion section 14. Stylet 26 includes elongate flexible sheath 28 adapted to be inserted into channel 22 of section 14, and bending mechanism 30 for bending the sheath. Sheath 28 is formed of a dense coil which is a little smaller in diametrical size and sufficiently longer than channel 22. A near distal end portion of sheath 28 is lower in coiling density than any other portion thereof, forming "weak-kneed" or additionally flexible bendable portion 28a. Rigid distal cap 32 is fixed to the distal end of sheath 28. Cap 32 includes cavity 33 fitted with the distal end of sheath 28 and distal end portion 34. Portion 34 has an oval cross section similar to and a little smaller than channel opening 22a of insertion section 14. When sheath 28 is inserted into channel 22, portion 34 of cap 32 is fitted in opening 22a to prevent the sheath from rotating. Cap 32 and opening 22a constitute positioning means for positioning sheath 28 relatively to insertion section 14.

Bending mechanism 30 for bending sheath 28 includes body 36 fixed to the proximal end of the sheath and slider 38 supported on the body so as to be slidable along the axis of the sheath. Finger ring 39 is attached to body 36. Operating wire 40 is inserted in sheath 28. One end of wire 40 is fixed to distal cap 32 by brazing in a manner such that it is biased to one end of the oval cap, with respect to the major axis thereof, in cavity 33 of the cap. The other end of wire 40 is drawn out from the proximal end of sheath 28 and fixed to slider 38. Thus, wire 40 is pushed or pulled by sliding the slider. When it is pulled, bendable portion 28a is bent in a direction to meet the eccentricity of the distal end of the wire, as indicated by two-dot chain line in FIG. 3.

More specifically, in bending bendable portion 28a of stylet 26, an operator first inserts the thumb of one of his hands into finger ring 39, and then holds slider 38 between the first and second fingers of the same hand. In this state, when slider 38 is retreated, operating wire 40 is drawn in to cause portion 28a of sheath 28 to be compressed and bent in the direction of deviation of the distal end of the wire. The bendable portion is straightened if slider 38 is pushed forward to force the wire in.

Using stylet 26 constructed in this manner, insertion section 14 of the endoscopic apparatus is bent in the following processes. First, sheath 28 of stylet 26 is inserted into channel 22 through inlet port 18 of operating section 12. Then, distal end portion 34 of distal cap 32 is fitted into channel opening 22a, as shown in FIG. 6. Cap 32 and opening 22a, which are both oval in shape, can engage each other only when they are oriented correspondingly. By fitting portion 34 of cap 32 into opening 22a, therefore, sheath 28 is prevented from rotating relatively to channel 22 and located for the alignment of the two oval configurations. In this state, by retreating slider 27 to bend bendable portion 28a of sheath 28, the distal end portion of insertion section 14 is bent in the same direction as portion 28a. Since the bending direction of portion 28a is restricted to the direction of the major axis of distal end portion 34 of cap 32, the distal end portion of section 14 is bent always in the direction of the major axis of channel opening 22a, as indicated by arrow A of FIG. 6. Preferably, the bending direction or major-axis direction A should not cross the axis of optical fibers of the image guide, light guide, etc.

In bending insertion section 14 in another direction, sheath 28 is drawn out of channel 22, and the whole stylet 26 is rotated 180 degrees around the axis of the sheath. Then, sheath 28 is inserted again into channel 22, and distal end portion 34 of distal cap 32 is fitted into channel opening 22a. Thus, the distal end portion of insertion section 14 can be bent in the opposite direction to the direction of arrow A.

According to the endoscopic apparatus constructed in this manner, the distal end portion of insertion section 14 can be bent accurately in the desired direction, and can hardly be bent in a direction to damage the optical fibers by mistake. Thus, endoscope body 10 can be improved in durability. Unlike the conventional one, moreover, the apparatus of the invention does not require any bendable portion, such as an articulated mechanism, in insertion section 14, so that the insertion section can be reduced in diameter. Sheath 28 of stylet 26 diminishes its bend angle, that is, becomes hard to bend, after prolonged use. In this case, only the sheath should be replaced or repaired without affecting the endoscope body. Thus, the apparatus is high in maintenance efficiency and in economical efficiency.

FIGS. 7 and 8 show a second embodiment of the present invention. According to this embodiment, sheath 28 and distal cap 32 have the same oval cross section. Likewise, channel 22 and channel opening 22a have an oval cross section. Accordingly, the position of sheath 28 relative to insertion section 14 can be restricted throughout the length of channel 22, so that the bending direction of the distal end portion of the insertion section can more securely be controlled. Since bendable portion 28a of sheath 28 also has an oval cross section, the distal end of operating wire 40 can be fixed with a sufficient eccentricity to the central axis of the sheath. Thus, sheath 28 can be bent easily. In this embodiment, moreover, channel opening 22a and the cross section of the distal end portion of cap 32 may be circular in shape.

In a third embodiment of the invention shown in FIGS. 9 and 10, sheath 28 of stylet 26 and distal cap 32 has a square cross section, and channel opening 22a is square, correspondingly. However, the cross section of channel 22 is, for example, circular so that sheath 28 can rotate in the channel.

According to the third embodiment, sheath 28 can be rotated relatively to channel 22 by only drawing out distal cap 32 from channel opening 22a without removing the whole sheath from the channel. Cap 32 can be fitted into opening 22a in any position at an angle corresponding to an integral multiple of 90 degrees to the position shown in FIG. 9. Thus, the distal end portion of insertion section 14 can be bent in both vertical and horizontal directions of FIG. 9. In this embodiment, channel 22 may be formed square in cross-sectional shape throughout its length.

Figure 11:
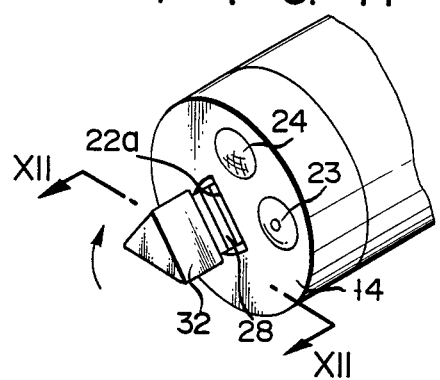
Figure 12:

In a fourth embodiment of the invention shown in FIGS. 11 and 12, sheath 28, distal cap 32, and channel 22 have a cross section shaped like an equilateral triangle. The distal end of operating wire 40 is fixed to a point near one of the vertexes of the triangle. According to this embodiment, the distal end portion of insertion section 14 can be bent in different directions at angular intervals of 120 degrees by changing the position of sheath 28 being inserted. If the cross section of channel 22 is shaped so that sheath 28 can rotate in the channel, the bending direction of the insertion section can be changed without drawing out the whole sheath from the channel.

The cross sectional shapes of the distal cap, channel, and channel opening are not limited to the ones described in connection with the above embodiments, and may be any configurations provided they allow the sheath to be nonrotatably positioned in the channel.

Figure 13:
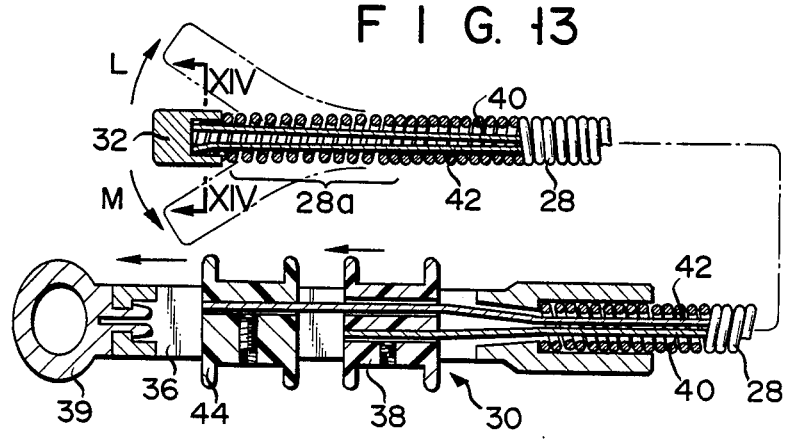
Figure 14:

FIGS. 13 and 14 show a fifth embodiment of the present invention. In this embodiment, stylet 26 includes second operating wire 42 as well as first wire 40. Like wire 40, wire 42 is inserted in sheath 28. The distal ends of wires 40 and 42 are fixed individually to the two ends of distal cap 32, as viewed in the direction of the major axis of the oval configuration of the cap. Bending mechanism 30 includes a pair of sliders 38 and 44 slidably supported on body 36. These sliders are fixedly spaced in their sliding direction. The rear end of wire 40 is fixed to slider 38, while that of wire 42 penetrates slider 38 to be fixed to slider 44.

According to this embodiment, bendable portion 28a of sheath 28 can be bent in the directions of arrows L and M of FIG. 13 by pulling sliders 38 and 44, respectively. Thus, with use of stylet 26 constructed in this manner, the distal end portion of the insertion section can be bent in two different directions with sheath 28 kept in the channel, that is, without changing the position of the sheath relative to the channel.

In the several embodiments described above, bending mechanism 30 is constructed so that the sheath is bent by pushing and pulling the operating wire or wires by means of the slider or sliders. Alternatively, however, it may be constructed as shown in FIG. 15.

In this sixth embodiment shown in FIG. 15, operating wire 40 is formed of a shape-memory alloy, such as titanium-nickel alloy, which contracts when heated to a temperature above room temperature, e.g., 50° C., and is restored to its original length when cooled. The distal end of wire 40 is fixed to distal cap 32, while its rear end is buried in body 36 of bending mechanism 30. Mechanism 30 includes control unit 46 for heating wire 40 to contract it. Unit 46 includes pulse current generator circuit 50 connected to the distal end of wire 40 by means of lead wire 48, and resistance measuring section 54 connected to the rear end of wire 40 by means of lead wire 52. Further, body 36 is provided with bend angle setting switch 56, which is connected to control circuit 58 of control unit 46. When a signal is applied to circuit 58 by switch 56, the circuit supplies an output signal to generator circuit 50. Thereupon, circuit 50 produces and supplies pulse current to wire 40 by way of lead wire 48. As a result, wire 40 is heated to contract, so that bendable portion 28a of sheath 28 of stylet 26 is bent in the direction of the arrow of FIG. 15. The resistance of wire 40 varies with its length or the curvature of sheath 28. If the curvature of the sheath becomes greater, then the resistance of wire 40 lowers in proportion. The resistance value is measured by resistance measuring section 54, and the measured value is applied to the input of control circuit 58. Circuit 58 compares the measured value with a bend angle set by switch 56. Based on the result of the comparison, it controls the pulse current from circuit 50. As a result, bendable portion 28a of sheath 28 is bent at a desired angle set by switch 56. When sheath 28 attains a desired curvature, its state is maintained by extending the power-off period or shortening the power-on period. Also, the bending speed of sheath 28 may be controlled by varying the off or on period.

The stylet with the above described construction can provide the same effects of the foregoing embodiments.

In the sixth embodiment, second operating wire 60 formed of a shape-memory alloy may be used in addition to wire 40, as shown in FIG. 16. Wire 60, along with wire 40, is inserted in sheath 28 so that its distal end is fixed to distal cap 32 at a position distant enough from the distal end of wire 40, and its rear end is buried in body 36. The distal end of wire 60 is connected to pulse current generator circuit 50 by means of lead wire 62, and its rear end to resistance measuring section 66 by means of lead wire 64. Section 66 measures the resistance of wire 60, and applies the measured value to control circuit 58.

According to stylet 26 constructed in this manner, bendable portion 28a of sheath 28 can be bent in two different directions by controlling pulse current supplied to wires 40 and 60. In FIGS. 15 and 16, like reference numerals refer to like members as in FIG. 3.

What is claimed is:

1. An endoscopic apparatus comprising:
   an operating section;
   a flexible insertion section extending from the operating section and adapted to be inserted into the body cavity and bent in a predetermined direction, said insertion section including a channel extending from the operating section to the distal end of the insertion section;
   a stylet including a sheath removably inserted in the channel and extending to the distal end of the insertion section, said sheath having a bendable portion located in the distal end portion of the insertion section, and operating means for remotely bending the bendable portion of the sheath from the operating section side to bend the distal end portion of the insertion section; and
   positioning means for positioning the bendable portion of the sheath in the distal end portion of the insertion section so that the bendable portion is bent in the predetermined direction.

2. The endoscope apparatus according to claim 1, wherein said channel has a cross section of non-circular configuration, and said sheath has a cross section similar to and a little smaller than that of the channel.

3. The endoscopic apparatus according to claim 2, wherein said channel has an oval cross section.

4. The endoscopic apparatus according to claim 2, wherein said channel has an equilateral triangular cross section.

5. The endoscopic apparatus according to claim 2, wherein said channel has a square cross section.

6. The endoscopic apparatus according to claim 1, wherein said operating means includes an operating wire inserted in the sheath and having one end fixed to the distal end of the sheath and the other end extending to the proximal end of the sheath, and means connected to the other end of the operating wire for pushing and pulling the wire.

7. The endoscopic apparatus according to claim 6, wherein one end of said operating wire is fixed eccentric, in one direction, to the central axis of the sheath.

8. The endoscopic apparatus according to claim 1, wherein said operating means includes an operating wire inserted in the sheath and having one end fixed to the distal end of the sheath and the other end extending to the rear end of the sheath, said operating wire being formed of a shape-memory alloy adapted to contract when heated and to be restored to its original shape when cooled to ambient temperature, and a control unit for heating the operating wire to control the length thereof.

9. The endoscopic apparatus according to claim 8, wherein said control unit includes a switch for setting the bend angle of the bendable portion of the sheath, a pulse current generator circuit for applying pulse current to the operating wire to heat the same, a resistance measuring section for measuring the value of resistance of the operating wire varying with the length of the wire, and a control section for driving the pulse current generator circuit in accordance with the bend angle set by the switch and the resistance value measured by the measuring section.

10. The endoscope apparatus according to claim 1 further including optical fibers in said flexible insertion section, said optical fibers including longitudinal axes, and said predetermined direction is spaced from said optical fibers whereby bending of said flexible section will not cause said bent flexible section to cross the longitudinal axes of said optical fibers.

11. The endoscope apparatus according to claim 10 wherein said sheath includes a coiled member with said coils being on a first pitch spacing in locations spaced from said bendable portion and on a second pitch spacing in said bendable portion, said second pitch spacing being larger than said first pitch spacing.

12. The endoscope apparatus according to claim 10 further including an illumination window in said insertion section and a viewing window in said insertion section, with a first plurality of said optical fibers being associated with said illumination window and a second plurality of said optical fibers being associated with said viewing window.

13. An endoscopic apparatus comprising:
an operating section;
a flexible insertion section extending from the operating section and adapted to be inserted into body cavity and bent in a predetermined direction, said insertion section including a channel extending from the operating section to the distal end of the insertion section;
a stylet including a sheath removably inserted in the channel and extending to the distal end of the insertion section, said sheath having a bendable portion located in the distal end portion of the insertion section, and operating means for remotely bending the bendable portion of the sheath from the operating section side to bend the distal end portion of the insertion section, the operating means including first and second operating wires inserted in the sheath and each having one end fixed to the distal end of the sheath and eccentric to a central axis of the sheath, and the other end extending to the rear end of the sheath, and means connected to the other ends of the first and second operating wires for pushing and pulling the wires; and
positioning means for positioning the sheath in the insertion section so that the bendable portion is bent in the predetermined direction.

14. The endoscopic apparatus according to claim 13, wherein one end of said second operating wire is fixed eccentric to the central axis of the sheath in the opposite direction to the direction of eccentricity of the first operating wire.

15. An endoscopic apparatus comprising:
an operating section;
a flexible insertion section extending from the operating section and adapted to be inserted into the body cavity and bent in a predetermined direction, said insertion section including a channel extending from the operating section to the distal end of the insertion section, said channel including a channel opening at the distal end of the insertion section, said opening having a non-circular configuration;
a stylet including a sheath removably inserted in the channel and extending to the distal end of the insertion section, said sheath having a bendable portion located in the distal end portion of the insertion section, and operating means for remotely bending the bendable portion of the sheath from the operating section side to bend the distal end portion of the insertion section; and
positioning means for positioning the sheath in the insertion section so that the bendable portion is bent in the predetermined direction, said positioning means including a distal cap fixed to the distal end portion of the sheath, said cap having a cross section similar to and a little smaller than the opening and removably fitted in the opening.

16. The endoscopic apparatus according to claim 15, wherein said channel opening is oval.

17. The endoscopic apparatus according to claim 15, wherein said channel opening is equilateral triangular.

18. The endoscopic apparatus according to claim 15, wherein said channel opening is square.

* * * * *